(12) United States Patent
Chen et al.

(10) Patent No.: US 7,175,600 B2
(45) Date of Patent: *Feb. 13, 2007

(54) SPHYGMOMANOMETER

(76) Inventors: Kun-Sung Chen, 9F, No. 78, Sec. 1, Kwang-Fu Rd., San-Chung, Taipei County (TW); Ying-Chao Lin, 9F, No. 78, Sec. 1, Kwang-Fu Rd., San-Chung, Taipei County (TW); Kuo-Hung Huang, 9F, No. 78, Sec. 1, Kwang-Fu Rd., San-Chung, Taipei County (TW); Shin-Lung Du, 9F, No. 78, Sec. 1, Kwang-Fu Rd., San-Chung, Taipei County (TW); Hsing Ouyang, 9F, No. 78, Sec. 1, Kwang-Fu Rd., San-Chung, Taipei County (TW); Yao Ouyang, 9F, No. 78, Sec. 1, Kwang-Fu Rd., San-Chung, Taipei County (TW)

( * ) Notice: Subject to any disclaimer, the term of this patent is extended or adjusted under 35 U.S.C. 154(b) by 193 days.

This patent is subject to a terminal disclaimer.

(21) Appl. No.: 10/982,794

(22) Filed: Nov. 8, 2004

(65) Prior Publication Data

US 2006/0047204 A1    Mar. 2, 2006

(30) Foreign Application Priority Data

Aug. 31, 2004   (TW)   ............................... 93213826 U

(51) Int. Cl.
*A61B 5/02* (2006.01)
(52) U.S. Cl. .................................... 600/490
(58) Field of Classification Search ............... 600/300, 600/301, 490–503, 481, 483, 485
See application file for complete search history.

(56) References Cited

U.S. PATENT DOCUMENTS

| 4,998,534 | A  | * | 3/1991 | Claxton et al. ............. 600/483 |
| 6,353,755 | B1 | * | 3/2002 | Oguma ....................... 600/547 |
| 6,447,457 | B1 | * | 9/2002 | Forstner et al. ............. 600/485 |
| 6,734,856 | B2 | * | 5/2004 | Ishikawa et al. ............ 345/440 |
| 6,905,464 | B2 | * | 6/2005 | Kawanishi et al. ......... 600/301 |
| 2002/0002342 | A1 | * | 1/2002 | Iijima et al. ................ 600/547 |
| 2003/0094055 | A1 | * | 5/2003 | Sunako et al. ............. 73/866.1 |
| 2003/0176796 | A1 | * | 9/2003 | Lin ............................ 600/485 |

* cited by examiner

*Primary Examiner*—Charles A Marmor, II
*Assistant Examiner*—Navin Natnithithadha
(74) *Attorney, Agent, or Firm*—Rosenberg, Klein & Lee

(57) ABSTRACT

A sphygmomanometer is disclosed. The sphygmomanometer mainly includes multiple power buttons and multiple memory buttons mounted thereon, and the power buttons and the memory buttons are disposed in a corresponding manner for communicating with one another. Through pressing one of the power buttons, a measurement value of blood pressure can be directly stored into a correspondingly memory area, and by pressing one of the memory buttons which is corresponding to that power button, the stored measurement value is recalled and displayed on the displaying screen. Therefore, the sphygmomanometer can be provided for more than two users and can also respectively memorize (store) individual measurement value of blood pressure for each user. Furthermore, a selecting switch for selectively inactivating any selected power button is provided so that secure storage of personal information is also ensured.

14 Claims, 4 Drawing Sheets

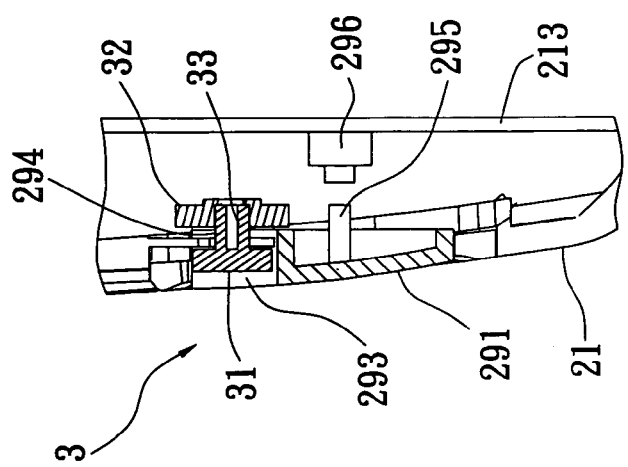
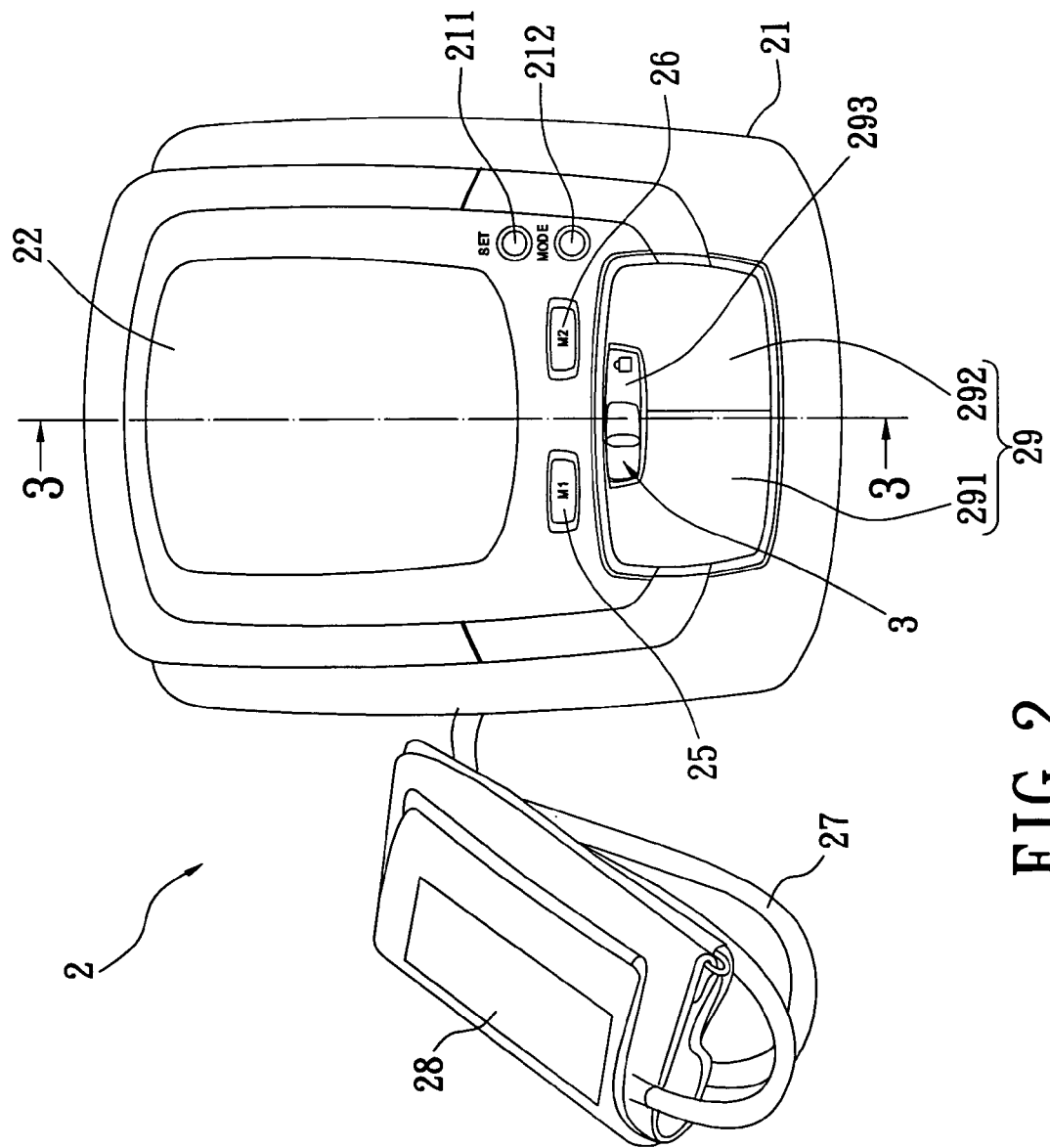
FIG. 3
FIG. 2

SPHYGMOMANOMETER

BACKGROUND OF THE INVENTION

1. Field of the Invention

The present invention relates to a sphygmomanometer, and more particularly to a sphygmomanometer which is provided for more than two users and also can respectively memorize individual results of each user's blood pressure, and which also takes into consideration the security of any information that is collected.

2. Description of Related Art

On account of their diet or lifestyle, aged people commonly suffer from cardiovascular diseases, and thus, often need to measure their blood pressure daily. To do this a sphygmomanometer is the preferred tool. Moreover, the patient has to then provide the results recorded and stored in the sphygmomanometer to their doctor for reference and diagnosis.

Referring to FIG. 1, a conventional sphygmomanometer comprises a main body 11 having an inner unit (such as a circuit component, an pneumatic component, etc.) mounted inside, a displaying screen 12 mounted on the main body 11, a power button 13 and a memory button 14 both mounted on the main body 11, a belt 16 which binds the arm of the user and a gas pipe 15 connected between the main body 11 and the belt 16, wherein the pneumatic component inside the main body 11 fills the belt 16 through the gas pipe 15 so as to tightly bind the belt 16 onto the user's arm. The displaying screen 12 displays all kinds of data and information including the measurement value of blood pressure. The power button 13 is used to turn on the conventional sphygmomanometer 1. The memory button 14 is used to recall the records of blood pressure stored in the machine's memory.

However, more than one person usually uses the same sphygmomanometer. Therefore, since the conventional sphygmomanometer 1 is designed to be used by only one person at a time, if the number of users who use the sphygmomanometer 1 is higher than one, then the recorded results become intermixed and are of no use to a doctor.

For solving the above defect, it is thought that the number of memory buttons 14 can be increased so that two (or more) users can separately store and recall their recorded results. However, this design still has some drawbacks because the user has to select which memory is the correct one to store the blood pressure every time they want to measure their blood pressure. For example, if A (B) user wants to select A (B) memory area, they have to press the A (B) memory button every time they measure their blood pressure. But, for the users, of whom almost all are elderly, this design is very inconvenient and hard to understand.

Furthermore, the security of the stored data must also be considered. That's because even though every user can patiently follow instructions to press the correct buttons during each operation, they will still encounter the following problems:

Although some user can patiently follow instructions, it cannot be guaranteed that another user will not choose to store their information in the incorrect place. For example, although user A has stored the data in memory area A, user B may incorrectly store their information in memory area A, thereby replacing user A's records, thus confusing the records and possibly leading to unfounded deductions by medical personal.

Consequently, a sphygmomanometer that can be used by multiple people, which is still easy to operate, and which also considers the security of information stored on it, is the aim of the present invention.

SUMMARY OF THE INVENTION

The objective of the present invention is to provide a sphygmomanometer which can be used by multiple users and the measurement value of each user can be stored individually, which is also convenient, hassle-free and difficult to store information on incorrectly, and which further ensures a user's information is stored in a secure manner.

For achieving the objective described above, the present invention provides a sphygmomanometer, comprising:

a main body having a displaying screen mounted thereon and an inner unit mounted therein;

a belt connected to the inner unit inside the main body through a gas pipe;

multiple power buttons mounted on the main body;

multiple memory buttons mounted on the main body; and a selecting switch mounted on the sphygmomanometer, the selecting switch is employed to control a selected power button to be inactivated, wherein the power buttons and the memory buttons have a corresponding number and are correspondingly disposed, and are all electrically connected to the inner unit; and through pressing one of the power buttons, a measurement value of blood pressure is directly stored into a correspondingly memory area of the inner unit, through pressing one of the memory buttons which is corresponding to one of the power buttons, the stored measurement value is recalled and displayed on the displaying screen, and by inactivating the selected power button by the selecting switch, access is denied to the memory area which corresponds to the selected power button.

BRIEF DESCRIPTION OF THE DRAWINGS

The foregoing aspects and many of the attendant advantages of this invention will be more readily appreciated as the same becomes better understood by reference to the following detailed description, when taken in conjunction with the accompanying drawings, wherein:

FIG. 2 is a three-dimensional drawing showing a sphygmomanometer according to the present invention;

FIG. 3 is an enlarged view showing a partial cross section of the sphygmomanometer in FIG. 2 according to the present invention;

DETAILED DESCRIPTION OF PREFERRED EMBODIMENTS

Figure 1:
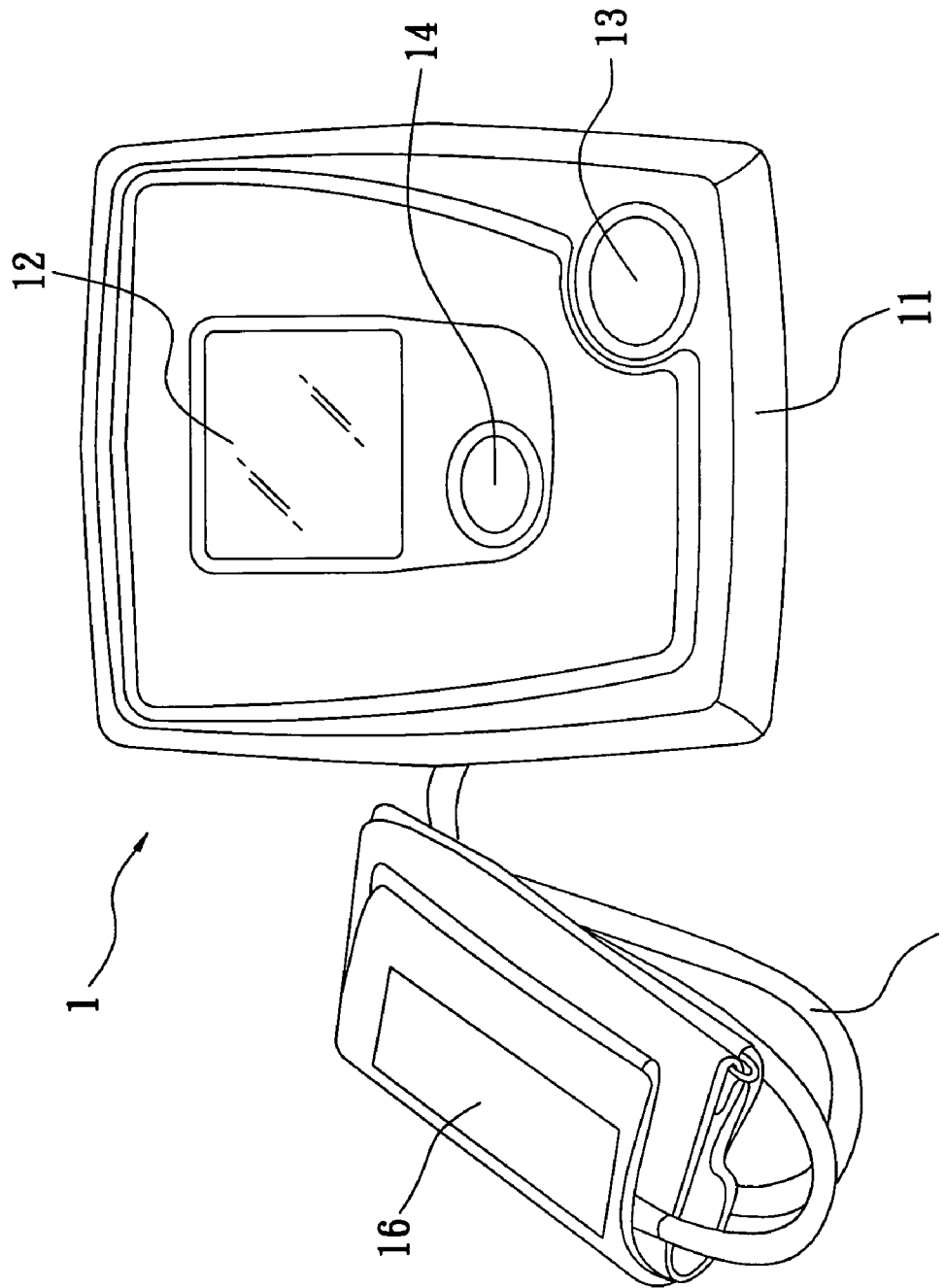
FIG. 1 is a three-dimensional drawing showing a conventional sphygmomanometer.
Figures 4, 5:
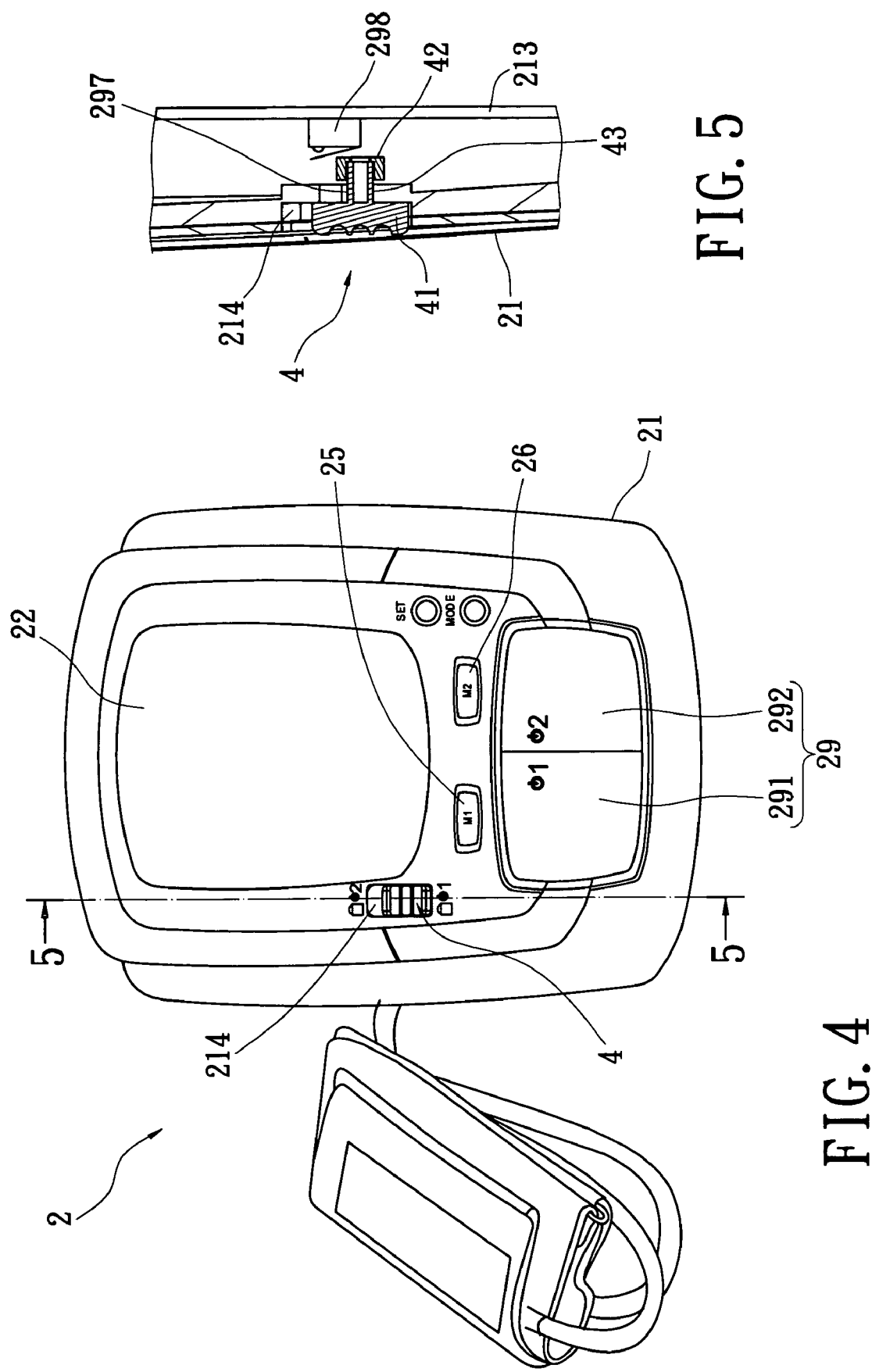
FIG. 4 is a three-dimensional drawing showing a selecting switch in a second preferred embodiment according to the present invention.
FIG. 5 is an enlarged view showing a partial cross section of the sphygmomanometer in FIG. 4 according to the present invention.

Please refer to FIGS. 2 and 3, which illustrate a sphygmomanometer 2 comprising a main body 21, a displaying screen 22, multiple power buttons 29 (in the present invention, comprising a first power button 291 and a second power button 292), a first memory button 25, a second memory button 26, a gas pipe 27, a belt 28 and a selecting switch 3, wherein the displaying screen 22 can be a LCD display and the main body 21 has an inner unit (not shown) (such as a circuit component, a pneumatic component etc.) mounted inside in a convenient place.

The belt 28 for binding the arm of the user is connected to the inner unit inside the main body 21 through the gas pipe 27 so as to fill the belt 28 with the pneumatic component of the inner unit.

The first and second power buttons 291 and 292 and the first and second memory buttons 25 and 26 are all mounted on the main body 21 and electrically connect with the inner unit. Furthermore, the first and second power buttons 291 and 292 and the first and second memory buttons 25 and 26 are disposed in a corresponding manner, wherein, as shown in FIG. 3, a respective inner side of the first and second power buttons 291 and 292 respectively has a rejecting body 295 mounted thereon and protruded outwardly. A plate body 213, which is located at the inner portion of the main body 21, has passive switches 296 respectively corresponding to each rejecting body 295 so that when the first or the second power button 291 or 292 is pressed, the rejecting body 295 triggers the passive switch 296 to conduct the first or the second power button 291 or 292. That is to say, the first and the second power buttons 291 and 292 are electrically connected to the inner unit through the passive switch 296. As such, an elastic element can be disposed between each power button 29 and passive switch 296, but this is omitted here and not shown in figures since, for one skilled in the art, it is easily understandable.

In addition, as shown to FIGS. 2, 4, 6 and 7, each power button 29 can individually turn on or turn off the sphygmomanometer 2. As to the selecting switches 3, 4 or 5, they are mounted on the sphygmomanometer 2 and can inactivate any selected power button 29.

Therefore, if a first user presses the first power button 291 to turn on the sphygmomanometer 2, then the measurement value of blood pressure will not only be displayed on the displaying screen 22, but will also automatically be stored into a first memory area (namely, the memory mounted in the inner unit) directly without requiring the user to select a memory area himself, and when a second user presses the second power button 292 to turn on the sphygmomanometer 2, identically, then the measurement value of blood pressure will not only be displayed on the displaying screen 22, but will also automatically be stored into a second memory area directly so that the results are respectively stored into different first and second memory areas without being intermixed and can be accessed the user or the doctor clearly and easily.

When the sphygmomanometer 2 is left unused for an extended period of time, or the first or second power button 291 or 292 is pressed, the sphygmomanometer 2 will be turned off and the first and second memory buttons 25 and 26 go into standby mode. Then, when the first user wants to review the values or show the values to his doctor, he only needs to correspondingly press the first memory button 25 to reveal his records on the displaying'screen 22. In other words, the second user may reveal the records on the displaying screen 22 by correspondingly pressing the second memory button 26. Through the above system, a sphygmomanometer which is convenient, hassle-free and difficult to store information on incorrectly is achieved.

According to the present invention, so that elderly people can easily understand that the person pressing the first power button 291 should be the same person who pressed the first memory button 25. Furthermore, so that their results can be easily recalled, each corresponding memory button is mounted at a position on the main body 21 corresponding to that of the power button.

Furthermore, each power button 29 is designed as a large button, which is far larger than the memory button, so that elderly people can easily and clearly recognize which power button 29 is used at the beginning of the process.

Moreover, the sphygmomanometer according to the present invention further has a setting button 211 and a mode-selecting button 212 mounted on the main body 21, and the setting button 211 and the mode selecting button 212 are both electrically connected to the inner unit inside the main body 21.

It should be noted that the number of the above-described first and second power buttons 291 and 292 and of the first and second memory buttons 25 and 26 are not limited to be two. There can be more than two so that more than two users may use the sphygmomanometer and the measurement value for each user may also be stored in the single sphygmomanometer. According to a first embodiment of the selecting switch: please refer to FIGS. 2 and 3, an indentation 293, having a hole 294 therein, is mounted between adjacent power buttons 29. The selecting switch 3 includes a switching body 31, which moves in a parallel manner (or in another manner) and is mounted in the indentation 293, an inner-edge portion 32 formed at an inner edge of the switching body 31 and extended into the main body 21, and a connecting body 33 connected between the switching body 31 and the inner-edge portion 32, wherein the connecting body 33 is penetrated through the hole 294 of the indentation 293, the indentation 293 may guide the movement of the switching body 31, and the inner-edge portion 32 of the selecting switch 3 contacts with an inside edge of the power button 29 thus locking the power button 29.

Thus, when the first user moves the switching body 31 of the selecting switch 3 (or through other methods) to a selected predetermined position, that is to say, a position which lets the inside edge of the power button 29 (in this case, the first power button 291) to be blocked by the inner-edge portion 32 so that the power button 29 can not be pressed down accordingly, it can therefore prevents a person accidentally pushing the button and further prevents previously stored data being overwritten. According to a second embodiment of the selecting switch: please refer to FIGS. 4 and 5, an indentation 214, having a hole 297 therein, is mounted on the main body 21. The selecting switch 4 includes a switching body 41 mounted in the indentation 214, and a control circuit (not shown) arranged in the main body 21 and electrically connected to the inner unit, whereby after the user makes a selection via the switching body 41, the control circuit may therefore control the electrical connection of the selected power button to be disconnected. Hence, any selected power button can be inactivated thereby.

Preferably, the selecting switch 4 further includes an inner-edge portion 42 formed at an inner edge of the switching body 41 and extended into the main body 21, a connecting body 43 connected between the switching body 41 and the inner-edge portion 42, and a passive switch 298 mounted on the plate body of the main body 21 and electrically connected to the control circuit, wherein the connecting body 43 is penetrated through the hole 297 of the indentation 214, the indentation 214 may guide the switching body 41 to be operated in a parallel movement manner, and the inner-edge portion 42 of the selecting switch 4 is corresponding to the passive switch 298.

Figure 6:
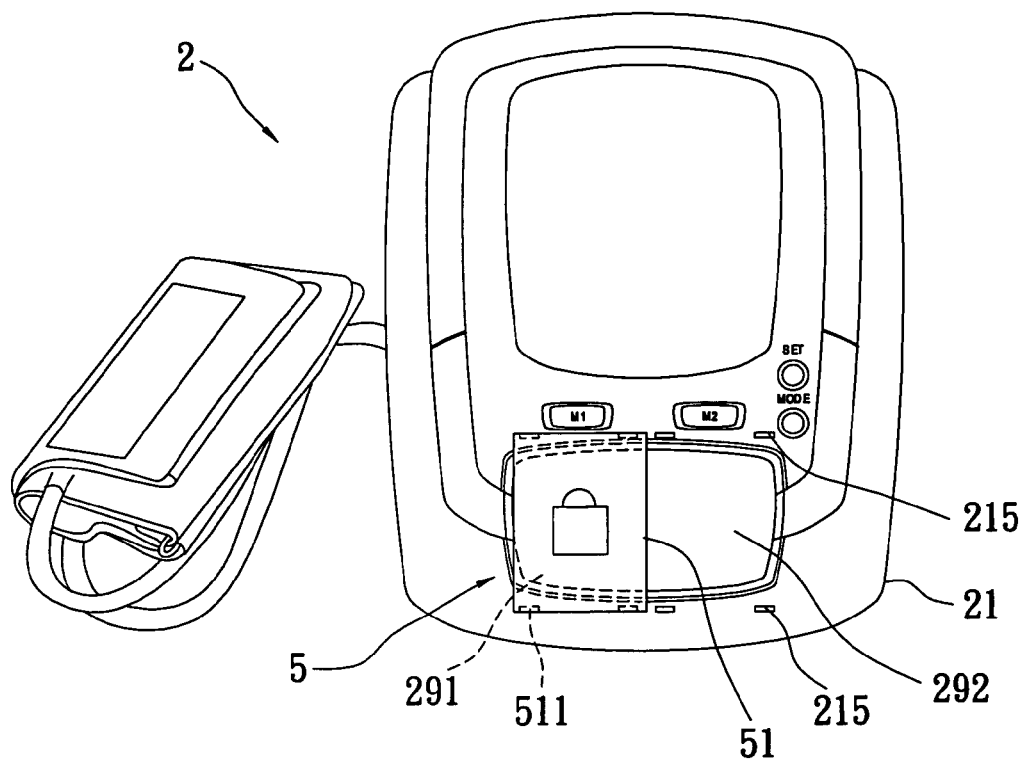
FIG. 6 is a three-dimensional drawing showing a selecting switch in a third preferred embodiment according to the present invention.
Figure 7:
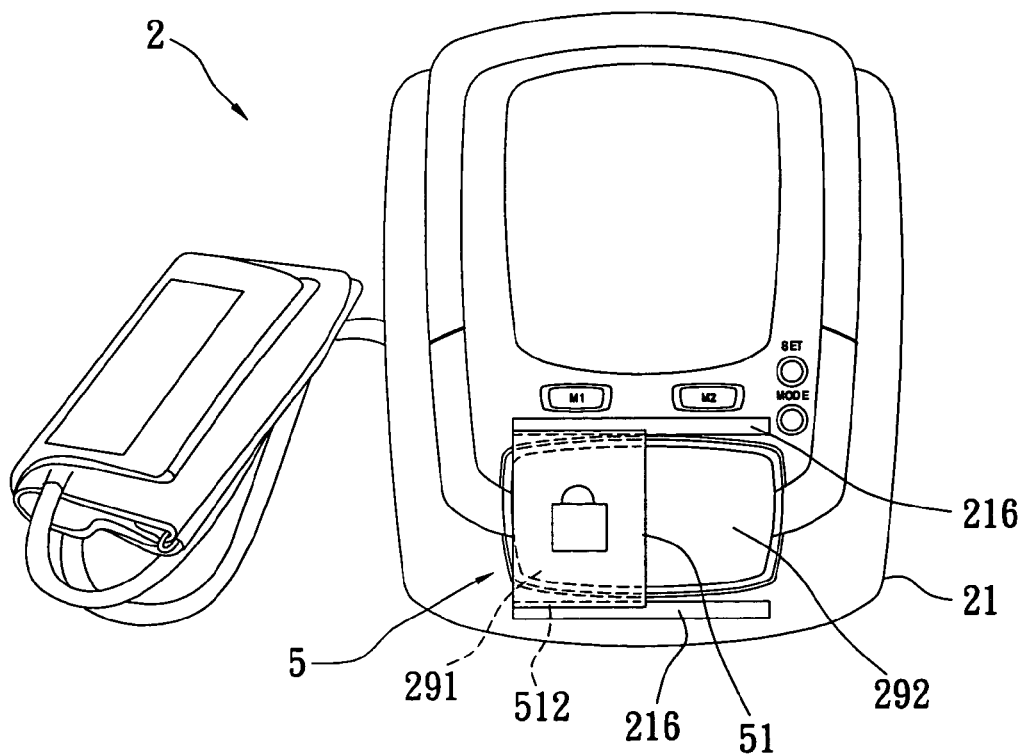
FIG. 7 is a three-dimensional drawing showing a selecting switch in a fourth preferred embodiment according to the present invention.

Therefore, when the first user moves the switching body 41 of the selecting switch 4 (or through other methods) to a selected predetermined position, it allows the passive switch 298 to be triggered, or not be triggered, which then generates two kinds of signals which are the basis for respectively inactivating the first or the second power button 291 or 292. The two signals generated by the passive switch 298 are transmitted to the control circuit for controlling the control circuit to respectively inactivate the first or the second power button 291 or 292 (in other words, disconnecting the power button). According to a third and a fourth embodiments of the selecting switch: please refer to FIGS. 6 and 7 showing the third and the fourth embodiments of the selecting switch. The selecting switch 5 also can be designed in a protective-cover fashion, wherein there are multiple positioning bodies 511, as shown in FIG. 6, or, as shown in FIG. 7, multiple guiding bodies 512, respectively mounted at the two opposite sides of the switching body 51, and on the main body of the sphygmomanometer 2, there are correspondingly multiple positioning holes 215, as shown in FIG. 6, or, as shown in FIG. 7, a sliding track pair 216, mounted thereon. Each positioning body 511 positions some positioning holes 215 to locate the selection (as shown in FIG. 6), or each guiding body 512 is slid along the sliding track pair 216, as shown in FIG. 7, to achieve the objective. Thus, when the user moves the switching body 51 according to the operation manner shown in FIG. 6 or FIG. 7 to cover the first power button 291, the first power button 291 can not depressed by the user. The first power button 291 is thereby protected and cannot be used, whereas the second power button 292 is protected and cannot be used.

Please refer to FIGS. 2, 4, 6 and 7. According to the present invention, a lock-on manner can also be employed for all the three kinds of selecting switches 3, 4 and 5 to notify the user that a power button is locked and can not be used. This is shown to the user at the two edges of the switching body 31 (FIGS. 2 and 3), at the main body 21 adjacent to the two edges of the indentation 214 (FIG. 4), and on the switching body 51 (FIGS. 6 and 7), and, additionally, on the displaying screen 22 (not shown).

In accordance with the structure described above, the sphygmomanometer according to the present invention can be used by multiple users and can individually store the measurement value lothereof so that the results are not intermixed with one another and can be clearly seen by the user or the doctor. Moreover, the sphygmomanometer according to the present invention is also advantageous in that it is convenient, not troublesome and difficult to operate incorrectly so that it is highly suitable for the elderly. Furthermore, the present invention ensures records are stored securely by selecting some power buttons to be inactivated, by which the corresponding memory area is also inactivated as well.

As can be seen from the above description, the sphygmomanometer according to the present invention, which exactly solves the defects in the prior arts, is a highly practical product which is also very efficient for everyone to use.

It is to be understood, however, that even though numerous characteristics and advantages of the present invention have been set forth in the foregoing description, together with details of the structure and function of the invention, the disclosure is illustrative only, and changes may be made in detail, especially in matters of shape, size, and arrangement of parts within the principles of the invention to the full extent indicated by the broad general meaning of the terms in which the appended claims are expressed.

What is claimed is:

1. A sphygmomanometer for use by more than one user, comprising:
    a main body having a displaying screen mounted thereon;
    an inner unit mounted inside the main body and including a memory;
    a belt connected to said inner unit through a gas pipe;
    a plurality of power buttons mounted on said main body, each of said power buttons for actuating said sphygmomanometer and storing of blood pressure measurement results;
    a plurality of memory buttons mounted on said main body, whereby actuation of one memory button recalls and displays said blood pressure measurement results on said displaying screen; and
    a selecting switch mounted on said sphygmomanometer, said selecting switch is employed to control a selected user's power button to be inactivated;
    wherein each of said power buttons has a corresponding memory button, all of said power and memory buttons being electrically connected to said inner unit,
    wherein actuation of said selected user's power button transmits a signal sent to said inner unit to initiate measurement and storing of blood pressure results into said memory, and
    wherein inactivating said selected user's power button by said selecting switch denies the storing of the blood pressure results to said memory.

2. The sphygmomanometer according to claim 1, wherein said power buttons comprise a first and a second power buttons, and said memory buttons comprise a first and a second memory button.

3. The sphygmomanometer according to claim 1, wherein each memory button is mounted at a position which corresponds to that of each power button, and each power button and each memory button are correspondingly communicated with one another.

4. The sphygmomanometer according to claim 1, wherein each power button is a large button whose size is far larger than that of said memory button.

5. The sphygmomanometer according to claim 1, wherein each power button and each memory button are in a one-on-one corresponding manner for communicating with one another.

6. The sphygmomanometer according to claim 1, wherein said main body further comprises a setting button and a mode selecting button mounted thereon and said setting button and said mode selecting button are electrically connected to said inner unit respectively.

7. The sphygmomanometer according to claim 1, wherein each of said power buttons is employed to individually turn on or turn off said sphygmomanometer.

8. The sphygmomanometer according to claim 1, wherein said selecting switch comprises a switching body mounted on said sphygmomanometer, and an inner-edge portion formed at an inner edge of said switching body, said inner-edge portion of said selecting switch being stopped at an inside edge of said power buttons so that after a position of said switching body is selected, said inside edge of said selected power button is blocked by said inner-edge portion and can not be used.

9. The sphygmomanometer according to claim 8, wherein said selecting switch further comprises an indentation formed between adjacent power buttons, a movement of said switching body being guided by said indentation.

10. The sphygmomanometer according to claim 8, wherein said selecting switch further comprises a connecting body connected between said switching body and said inner-edge portion, said connecting body being penetrated through said sphygmomanometer.

11. The sphygmomanometer according to claim 1, wherein said selecting switch comprises a switching body mounted at said main body and a control circuit arranged in said main body and electrically connected to said inner unit, whereby said control circuit is activated by a position selection of said switching body so that an electrical connection of said selected power button is disconnected accordingly.

12. The sphygmomanometer according to claim 11, wherein said selecting switch further comprises an inner-edge portion formed at an inner edge of said switching body and extended into said main body, and a passive switch mounted at said main body and electrically connected to said control circuit, whereby after said position selection of said switching body makes said inner-edge portion act on said passive switch so as to activate said control circuit, said electrical connection of said selected power button is disconnected accordingly.

13. The sphygmomanometer according to claim 1, wherein said selecting switch is a selecting switch in a protective-cover fashion and has plural positioning bodies, and also comprises plural positioning holes mounted on said main body, wherein each positioning body is employed to position a random positioning hole of said positioning holes so as to cover and therefore inactivate said selected power button by said switching body.

14. The sphygmomanometer according to claim 1, wherein said selecting switch is a selecting switch in a protective-cover fashion and has plural guiding bodies, and also comprises a sliding track pair mounted on said main body, wherein each guiding body of said selecting switch is slid in said sliding track pair so that said switching body is slid to cover and therefore inactivate said selected power button.

\* \* \* \* \*